United States Patent [19]

Brem

[11] 4,180,058

[45] Dec. 25, 1979

[54] METHOD OF TREATING PATHOLOGICAL CONDITIONS OF THE NAIL

[76] Inventor: Jacob Brem, 11 Eaglehead St., Shrewsbury, Mass. 01545

[21] Appl. No.: 933,820

[22] Filed: Aug. 15, 1978

[51] Int. Cl.$^2$ ............................................. A61B 17/00
[52] U.S. Cl. ............................... 128/1 R; 128/329 R
[58] Field of Search ............... 128/1 R, 153, 172, 303, 128/303.1, 305.1, 333, 336, 260, 329 R, 305

[56] References Cited

U.S. PATENT DOCUMENTS 3,766,923  10/1973  Boretos .............................. 128/329

OTHER PUBLICATIONS

"Nails and Fungi," *British Journal of Dermatology*, 94,697 (1976).
Moschella et al., *Dermatology*, W. B. Saunders, Chapter 13 (1975) p. 622.
Zaias, "Onchomycosis," Arch. Dem. vol. 105, pp. 263–274 (Feb. 1972).
Jones, "Imidazoles Seen Closest to Ideal Antifungal Agent," *Skin and Allergy News* (2/78).
Moshella et al., *Dermatology*, L. A. Norton, "Disorders of the Nails," chp. 26, p. 1222.
"Dealing with an Infected Toenail," Worcester Telegram, Apr. 6, 1978, Johnson.
Vanderdonckt et al., "Miconazole Alcoholic . . . Infections," Mykosen 19(7) pp. 251–256 Sep. 1975.

*Primary Examiner*—Willis Little
*Attorney, Agent, or Firm*—Sewall P. Bronstein

[57] ABSTRACT

A method for treating pathological conditions of the nail, particularly onychomycosis, is described. The method comprises the breaching the protective keratin of the nail to form an opening therein, placing a caustic-keratolytic agent in the opening to enlarge it, and treating the nail through the opening with topical therapeutic agents for the pathological condition being treated, for instance, an antifungal agent for onychomycosis. In addition, thick callouses and painful plantar warts can be removed with modifications of this method.

13 Claims, 4 Drawing Figures

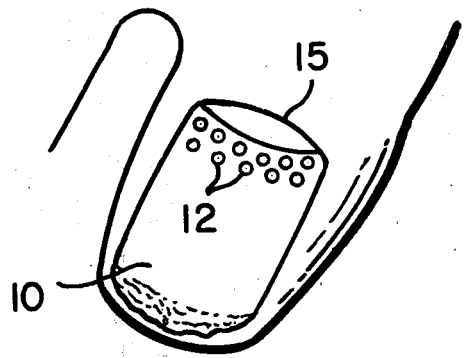

METHOD OF TREATING PATHOLOGICAL CONDITIONS OF THE NAIL

FIELD OF THE INVENTION

This invention is related to methods for treating pathological conditions of the nail that cause thickness, enlargement, and deformity of the nail, particularly methods for treating onychomycosis. It enables the therapeutic agent to reach conditions and parasites, hitherto protected by hard keratin.

BACKGROUND OF THE INVENTION

Human nails support a surprisingly varied fungal flora, including not only dermatophytes and yeasts, but many mold species both common and uncommon. These infections are known by two names, onychomycosis and tinea unguium. Onychomycosis literally means "fungus infection of the nail," where "tinea" is an ancient word for "ringworm."

Three groups of fungi are involved in onychomycosis: the dermatophytes, the molds and the yeasts. An attempt to account for the various clinical manifestations of onychomycosis by considering the requirements of these groups of fungi was made by English in "Nails and Fungi", *British Journal of Dermatology*, 94, 697 (1976).

Invasion of the nail apparatus by fungi produces changes of varying degree which are indistinguishable in respect to the causative fungus. A variety of other dermatoses affect nail growth and are frequently misdiagnosed as fungal infections. However, the clinical features of these nail conditions are ordinarily sufficient to distinguish them. The fungus which causes nail infections most commonly is *T. rubrum*. Next in importance is *T. mentagrophytes*, though it infects the toenails most commonly, rarely the fingernails. Other species of dermatophytes, including members of the genera Microsporum and Epidermophyton, cause nail infections uncommonly, with the possible exception of *T. violaceum*, which has been reported as the responsible agent in fingernail infections by observers in some Far Eastern countries. Candidiasis of the nails is another condition which occurs most frequently in individuals with immuno-deficiency diseases.

Ringworm infections of the toenails are an exceedingly common condition in races accustomed to wearing shoes. It is almost inevitable in persons who have had recurrent attacks of athlete's foot or who suffer from the chronic squamous type of foot ringworm caused by *T. rubrum*. It is encountered most frequently in adult males, though it is by no means uncommon in females. Ringworm of the toenails has been considered of little medical importance, since it causes no subjective distress unless the distortion is very marked, with resultant impingement of the nail margin of the soft tissues. The role of chronic infections of nails upon the general health of the individual has not been determined. Most authorities agree that it is a public health problem and it would be beneficial to eradicate the parasite. There is always the possibility that a fungal infection of the nail may act in a synergistic way in allowing pathogenic microbial agents to invade the body.

Ringworm infections of the nail organ vary greatly in their manifestations, from changes which are hardly detectable to the full-blown infection in which the nail plate is almost completely replaced by hard amorphous tissue (keratin). The infection may be entirely confined to the lateral nail groove (gutter of nail), failing to invade the substance of the nail plate at all, or doing so to a very trivial degree. This is the most minor expression of ringworm of the nail organ, and it is usually overlooked.

Further extension of the infection occurs from the lateral grooves underneath the lateral borders of the nail into the keratin produced by the nail bed. It then extends upward into the lower surface of the nail plate. The infection frequently becomes static at this point, progressing no further over a period of years, and resulting only in white or yellow discoloration and minor disorganization of the involved portion of the nail plate. If the affected zones are firm and intact, the changes do not ordinarily cause much concern to the patient.

With further progression of the disease, the fungus extends farther into the lower portion of the nail plate, and a disturbance of the nail bed results, transforming it into a thickened membrance which synthesizes keratin rapidly. This stimulation of the nail bed epithelium to produce soft keratin is the most characteristic change in well-defined ringworm infections of the nail, since it produces an accumulation of variable amounts of subungual hyperkeratosis. This change may, however, be produced in other diseases and is not pathognomonic for ringworm infection. The fungus proliferates abundantly in this subungual mass, serving as a mycotic reservoir for extension of the infection farther into the nail plate and to other nails and to other individuals. The progression from this point on is variable. The fungus possesses an enzyme (keratinase) which splits the nail allowing further spread of infection. The nail bed may become very hyperkeratotic, lifting up and separating the nail plate. The keratinous debris may fuse with the over-riding nail plate and give the impression that the nail itself is greatly thickened. The nail may reach a thickness of 8 mm. Normally the thickness of the toenail is about 2 mm. The patient is unable to cut the nail. The end becomes irregular and jagged, and one has to resort to filing the nail.

The nail matrix also becomes involved and the lunula usually present in the large toenail disappears. The destructive changes in the nail occur after it is formed, not because of any primary disturbance in its growth. In some instances the nail plate may be very widely separated from the bed, and the curved nail becomes troublesome mechanically. Destruction of the nail plate usually occurs distally in the beginning, but may extend all the way to the proximal portion.

The treatment of onychomycosis to date is difficult. Most physicians make no attempt at treatment because hitherto there has not been any acceptable method of therapy for toenails. Systemic treatment with griseofulvin may be curative, but the drug must be taken for a period of ten to twelve month or longer, and may give rise to side effects. Even then little affect is usually noticed on badly infected toenails. Even when cure is apparent reinfection commonly occurs, particularly in plantar and interdigital tinea pedis cases.

The two volume text book *Dermatology*, by Moschella, et al., W. B Saunders, (1975), Chapter 13—"Superficial and Deep Mycotic Infections" at page 662 states that topical antifungal compounds are completely ineffective in reversing the changes and do not have any demonstrable effects in preventing progression of the infection. This is because the primary site of infection is under the nail plate.

The best treatment for nondermatophytic onychomycosis is avulsion which is curative in a majority of cases. This is the apparent conclusion of Dr. Zaias in "Onychomycosis", *Arch. Derm.*, Vol. 105, pp. 263-274 (February 1972) who stated at page 273 of said article that there is no effective topical drug available at present. Even avulsion of the nail plate alone will not result in cure of fungal infections of the toenail, but must be accompanied by treatment with griseofulvin to afford complete cure.

As recent as February 1978, in an article "Imidazoles Seen Closest to Ideal Antifungal Agent" in Skin & Allergy News at page 58 it is reported that Dr. Herny E. Jones, chairman of dermatology at the Emory University School of Medicine, Atlanta, said that no topical agents will treat onychomycosis or tinea capitis and griseofulvin must be used against those infections for which topical antifungals are useless.

Avulsion of the infected toenail, i.e., surgery, is traumatic and results in loss of the nail if the matrix is removed or frequently, recurrence if the matrix is not removed. Long term treatment with griseofulvin also is not very effective for infections of the toenail. Therefore, it is still highly desirable to achieve an effective topical treatment for onychomycosis.

SUMMARY OF THE INVENTION

I have now discovered that an effective treatment by topical agents for pathological conditions of the nail comprises:

(1) breaching the keratin of the nail to form an opening therein;

(2) placing caustic-keratolytic agent in the opening to enlarge the opening; (and at the same time causing some destruction of fungal colonies); and (3) treating the nail through said opening with a topical specific therapeutic agent for said pathological condition.

In a preferred embodiment, onychomycosis is treated by drilling a number of holes across the nail in the form of a crescent, each hole being drilled in close proximity to the cuticle. The caustic-keratolytic agent is applied and then the nail is treated daily with an antifungal agent. Preferably the antifungal agent also has keratolytic action. Each week, or more often, an additional series of holes is drilled across the nail in a crescent shape more distal to the cuticle and between the holes in the previous series. After each new series of holes is drilled, all of the holes are again treated with the caustic-keratolytic agent and then daily with a keratolytic and antifungal agent. At each visit (periodic intervals of a week or less), the previous holes are enlarged with the caustic-keratolytic agent and new holes are drilled. As the nail begins to heal, the lunula makes its appearance. With growth of the nail, the peripheral part is cut away until a normal nail appears. The process is slow because it depends on the normal rate of nail growth and generally takes about 12-18 months to obtain a normal nail.

In another preferred embodiment of my invention, a very thick nail can be avulsed without anesthesia by drilling a network of holes over the entire nail, treating the nail with a caustic-keratolytic agent to enlarge the holes and treating the nail with a proteolytic enzyme such as papain. Preferably the proteolytic enzyme is applied as a solution by a wet dressing which is kept on the nail overnight. After two or three applications the nail can be avulsed without pain to the patient.

In yet another embodiment of my invention, thick callouses and plantar warts can be removed by drilling holes into the callouses or warts and following with treatments as outlined above.

By the term "caustic-keratolytic agent" as used herein I mean a caustic agent that lyses the keratin of the nail. Typically such agents cause destruction of the tissue at the site of application and also destroy fungi.

DETAILED DESCRIPTION OF THE INVENTION

Figure 1:
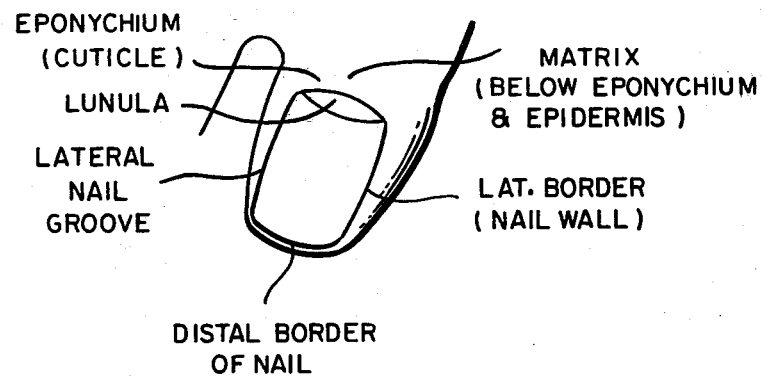
FIG. 1 illustrates the landmarks of a normal right toenail.

In accord with the present invention, an effective method for the topical therapeutic treatment of pathological conditions of the nail, particularly onychomycosis, is provided. The method is characterized by breaching the protective keratin of the nail and rendering the parasite vulnerable to treatment by topically applied therapeutic agents. A caustic-keratolytic agent is used to promote the breaching of the keratin thus facilitating the penetration of the therapeutic agent and increasing the exposure of the condition to the topical agent. The method is not too painful or traumatic and can be accomplished without administering anesthesia.

In a preferred embodiment of this invention, an infected nail is prepared for treatment by thorough cleaning. Any commonly accepted cleaning treatment for preparing a surface for surgery can be used. An acceptable preparation for purposes herein comprises thorough washing with soap and water followed by the liberal application of 70% isopropyl alcohol. Any equivalent preparation may be used.

Next, referring to the drawings, holes 12 are drilled in the nail 10 in the form of a crescent about 2 mm distal to the cuticle 15, particuarly along the area where the lunula is present. The holes are preferably first started with a sterile 18 or 20 gauge needle and then enlarged with a Bunnel drill using, for example, an excavating dentist drill. Any other suitable means for drilling holes in the nail can be substituted. No anesthesia is necessary. However, caution must be exerted when drilling these holes. The nail plate may vary in thickness and the nail bed is highly vascular and innervated. Thus, the patient may experience some transitory sharp pain when the nail bed is reached.

The size and spacing of the drilled holes (12) is dependent upon many parameters, including the size of the nail, particularly the width and thickness of the nail, and the rate of growth of the particular nail under treatment. Generally, a drill hole having a diameter of from about 1 to 2 mm with about 2 mm between the holes in each series is satisfactory. The number and size of the drill holes is best determined by the practitioner administering the treatment in each individual case and will vary depending upon the age, health and tolerance of the patients. For an average size toenail, approximately 4 to 8 holes in the initial series is generally quite adequate for beginning treatment in accord with this invention depending upon the size of the nail. The drillings brought up are useful for KOH examinations, culture and histological examination.

After drilling the holes, a caustic-keratolytic agent is applied to each hole to enlarge the hole and break down the keratin so that the antifungal agent can spread toward the colonies of the fungi. It is believed that the caustic-keratolytic agent broadens the holes to expose and treat more of the infected area of the nail. A satisfactory method for applying the caustic-keratolytic agent has been found to be accomplished by dipping a round toothpick in the caustic-keratolytic agent and applying it to the hole by means of a to and fro rolling motion of the toothpick between the thumb and the index finger. However, other suitable methods can readily be substituted by those skilled in the art.

Any substance having caustic-keratolytic action can be used as the agent. Dichloracetic acid has been used successfully and is presently preferred. Other suitable caustic-keratolytic agents useful in the practice of this invention include, for example, glacial acetic acid, mono and trichloracetic acid, podophylum, podophylum resin, exsiccated alum, benzoic acid, salicylic acid, resorcinol, and various thiols. All of the above also have antifungal properties.

After the holes are drilled and treated with the caustic-keratolytic agent, the nail is treated daily, particularly in the area of the holes, by topical application of the indicated therapeutic agent, an antifungal agent in the case of onychomycosis. Preferably, the therapeutic agent is applied twice a day by a rubbing motion.

Any suitable antifungal agent can be used for treating onychomycosis. A particularly useful antifungal agent is an ointment containing 3% by weight sulfur precipitated and 3% by weight salicylic acid in petrolatum, and this ointment is presently preferred for the treatment of onychomycosis. However, there are many antifungal agents that are useful in the practice of this invention. Examples of such antifungal agents include Miconazole, Nitrate (2%) cream or lotion, Haloprogin (1%) cream or solution, glutaraldehyde, Thiabendazole cream (10%), Mycostatin cream, ointment or powder, griseofulvin (2%) cream, ung. or lotion, Flucytosine ung. or cream, Ancolon, Fungizone cream, lotion or unguentum, Tinaftate, Tinactin (17%) cream, solution or powder, Clotrimazole cream or solution, and like antifungal agents.

It has been found that covering the ointment with a gauze dressing enhances the effect of this ointment.

In treating pathological conditions of nails, other than onychomycosis, such as, for instance, psoriasis of nails, atopic eczema, contact eczema, hypertrophy and painful deformity of nails due to aging or chronic trauma, other suitable topical therapeutic agents can be applied such as, for instance, fluorinated and non-fluorinated steroids, coal tar preparations, and the like, the particular agent being readily selected by those skilled in the art depending on the particular pathologic condition being treated.

At periodic intervals an additional series of holes is drilled distally to the previously drilled holes. At such periodic intervals each hole is again treated with the caustic-keratolytic agent to facilitate spreading of the therapeutic agent throughout the nail. New series of holes are drilled after each predetermined period, such as weekly or more often, if possible, until a network of holes covers the nail or until the healthy new growth of nail extends at least 2 mm distal from the cuticle.

Treatment with the therapeutic agent or antifungal agent is continued daily until a full healthy nail is grown. Generally, about 12 to 18 months is required to obtain a normal toenail.

Figures 2A, 2B:
FIG. 2A illustrates a right infected, thickened toenail in which a first series of holes have been drilled to begin treatment in accord with a preferred embodiment of this invention.
FIG. 2B illustrates a nail in which a second series of holes have been drilled after the first treatment in accord with a preferred embodiment of this invention.
Figure 2C:
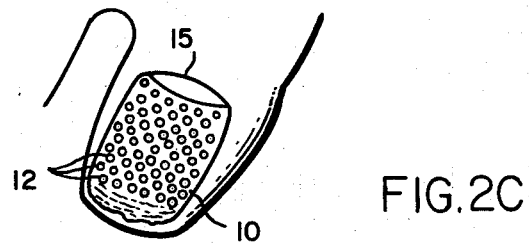
FIG. 2C illustrates a right infected, thickened toenail in which a network of holes have been drilled in accord with a preferred embodiment of this invention.

In another embodiment of my invention painful hypertrophied nails due to chronic trauma or psoriasis can be avulsed. A network of holes is drilled all over the nail as illustrated in FIG. 2C. The nail is then treated with a caustic-keratolytic agent as described above to enlarge the holes. The nail is then covered with a dilute solution, preferably containing about 1 to 5 percent by weight, of a proteolytic enzyme as a wet dressing. The dressing is preferably kept on for at least eight hours, most preferably overnight. Typically, after 2 or 3 applications of the proteolytic enzyme solution, the nail plate can be avulsed without pain to the patient and without injury to the matrix.

The function of the proteolytic enzyme is thought to be the breaking of peptide bonds in the keratin of the nail. Any known proteolytic enzyme is suitable for this purpose. Papain is presently preferred. The enzyme can also be applied as a cream or lotion.

A patient treated by the method described herein had contracted onychomycosis ten years earlier. The infection involved the nails of both large toes, both fifth toes, the right fourth toe, and the right thumb. Although the infection had been asymptomatic for several years, the patient sought advice of his physician and was treated systemicly with griseofulvin for one year with the result that the nail of the right thumb was cleared, but the nails of the involved toes remained thickened, yellowish-brown, exhibited loss of transparency, and the nails of both fifth toes became curved and turned upward.

The patient was then treated in accord with the present invention by drilling from 4 to 8 holes in each nail, depending upon the size, and treating with dichloracetic acid as the caustic-keratolytic agent, and then twice daily application of an ointment containing 3% sulfur ppt. and 3% salicylic acid in petrolatum. It should be noted that the preferred antifungal agent (the ointment described above), itself, acts as a keratolytic agent, an antifungal agent and an antimicrobial agent to prevent bacterial infection in the newly breached openings of the nail. After approximately 8 months, full healthy nails replaced the infected nails. No recurrence of the infection is evident, to date.

I have also discovered that the above methods for treating pathological conditions of the nail are useful in the treating of thick callouses and plantar warts. Holes are drilled in the callous or plantar wart, followed by topical treatment to destroy the unwanted tissue. This can be accomplished by treatment with wet dressings of a proteolytic enzyme as described above or other known treatments presently used by skilled professionals in the art. The use of holes dramatically increases the progress of treatment. This invention has been described in detail with particular reference to the preferred embodiments thereof. However, it is readily appreciated that, from reading this disclosure, modifications within the spirit and scope of the invention may be effected by those skilled in the art.

I claim:

1. A method for the treatment of a pathological condition of the nail, said method comprising the steps of breaching the keratin of the nail to form an opening therein, placing a caustic-keratolytic agent in said opening to enlarge the opening, and treating the nail through said opening with a topical therapeutic agent for said pathological condition.

2. A method in accord with claim 1 wherein said step of breaching the keratin includes drilling holes in the nail in close proximity and distally to the cuticle.

3. A method in accord with claim 2 wherein the treatment is initiated by drilling about 4 to 8 holes having a diameter of about 1 to 2 mm in said nail, the holes being about 2 to 4 mm apart.

4. A method in accord with claim 1 wherein said step of breaching the keratin includes initially drilling a series of holes in close proximity to the cuticle of the nail and periodically thereafter drilling new series of holes between the last drilled series and the distal end of the nail until the nail is covered with a network of holes, all holes being treated with said caustic-keratolytic agent when each new series of holes is drilled, and the nail being treated daily with said topical therapeutic agent.

5. A method in accord with claim 4 wherein each said series of holes is drilled in a crescent shape.

6. A method in accord with claim 1 wherein said pathological condition is onychomycosis and said topical therapeutic agent is an antifungal agent.

7. A method in accord with claim 6 wherein said step of breaching the keratin includes initially drilling a series of holes in a crescent shape in close proximity to the cuticle of the nail and weekly thereafter drilling new series of holes distally between the last drilled series and the edge of nail until the nail is covered with a network of holes, all holes being treated wlith said caustic-keratolytic agent when each new series of holes is drilled, and the nail being treated daily with said antifungal agent.

8. A method in accord with claim 7 wherein each series of holes comprises about 4 to 8 holes having a diameter of about 1 to 2 mm and spaced about 2 to 4 mm apart.

9. A method for avulsing a hypertrophied nail comprising drilling a network of holes over the entire nail, treating the nail with a proteolytic enzyme, and avulsing the nail.

10. A method of claim 9 wherein the treating step comprises applying the proteolytic enzyme as a dilute solution by a wet dressing.

11. The method of claim 10 wherein said proteolytic enzyme is present in the solution in a concentration of about 1 to 5 percent by weight.

12. The method of claim 9 wherein said proteolytic enzyme is papain.

13. A method for removing a callous or plantar wart comprising drilling at least one hole in said callous or plantar wart, followed by topical treatment to destroy the unwanted tissue.

* * * * *